(12) United States Patent
Greco et al.

(10) Patent No.: US 9,757,285 B2
(45) Date of Patent: Sep. 12, 2017

(54) ABSORBENT ARTICLE INCLUDING A BUFFER COMPOSITION

(75) Inventors: Joseph Greco, Morristown, NJ (US); David Gubernick, Cherry Hill, NJ (US); Claudia Massiel Montoya, Princeton, NJ (US)

(73) Assignee: Edgewell Personal Care Brands, LLC, Chesterfield, MO (US)

( * ) Notice: Subject to any disclaimer, the term of this patent is extended or adjusted under 35 U.S.C. 154(b) by 73 days.

(21) Appl. No.: 13/041,660

(22) Filed: Mar. 7, 2011

(65) Prior Publication Data

US 2012/0232510 A1 Sep. 13, 2012

(51) Int. Cl.
*A61F 13/84* (2006.01)
*A61F 13/534* (2006.01)
*A61F 13/537* (2006.01)
*A61F 13/513* (2006.01)
*A61F 13/53* (2006.01)

(52) U.S. Cl.
CPC .... *A61F 13/8405* (2013.01); *A61F 13/51394* (2013.01); *A61F 2013/530554* (2013.01); *A61F 2013/530678* (2013.01); *A61F 2013/8411* (2013.01); *A61F 2013/8497* (2013.01)

(58) Field of Classification Search
CPC ...... A61F 13/8405; A61F 2013/530678; A61F 13/51394; A61F 13/51496; A61F 2013/15243; A61F 2013/427; A61F 2013/51377; A61F 2013/530532; A61F 2013/530547; A61F 2013/530554; A61F 2013/8411; A61F 2013/8497
USPC .......... 604/359, 360, 375, 378, 367
See application file for complete search history.

(56) References Cited

U.S. PATENT DOCUMENTS

| 5,525,346 A | * | 6/1996 | Hartung et al. ............ 424/402 |
|---|---|---|---|
| 5,891,120 A | * | 4/1999 | Chmielewski ............... 604/378 |
| 6,459,014 B1 | | 10/2002 | Chmielewski et al. |
| 7,163,528 B2 | * | 1/2007 | Christon .......... A61F 13/15203 604/385.01 |
| 7,323,615 B2 | | 1/2008 | Gustavsson et al. |
| 8,292,864 B2 | * | 10/2012 | Hood ............... A61F 13/15203 604/378 |
| 2005/0215962 A1 | * | 9/2005 | Litvay ................ A61F 13/5323 604/358 |
| 2006/0129116 A1 | * | 6/2006 | Hughes ............ A61F 13/47254 604/361 |
| 2006/0264857 A1 | | 11/2006 | Colbert |
| 2009/0041697 A1 | | 2/2009 | Klofta et al. |
| 2009/0275906 A1 | | 11/2009 | Berland et al. |
| 2009/0306612 A1 | * | 12/2009 | Husmark .......... A61F 13/8405 604/360 |

(Continued)

FOREIGN PATENT DOCUMENTS

| EP | 1034803 A1 | 9/2000 |
|---|---|---|
| EP | 1358894 A1 | 11/2003 |
| EP | 1455712 B1 | 8/2006 |

(Continued)

*Primary Examiner* — Lynne Anderson
(74) *Attorney, Agent, or Firm* — Edgewell Personal Care Brands, LLC (57) ABSTRACT

The present invention generally relates to absorbent sanitary articles for absorption of body fluids and in particular to a sanitary article of this type including a buffer composition adapted to adjust the natural pH of the absorbed body fluid to a pH that is compatible with the pH of skin.

18 Claims, 4 Drawing Sheets

(56) References Cited

U.S. PATENT DOCUMENTS

| | | |
|---|---|---|
| 2010/0042062 A1 | 2/2010 | Fernkvist et al. |
| 2012/0004632 A1* | 1/2012 | Zhang .................... A61F 13/53 604/372 |

FOREIGN PATENT DOCUMENTS

| | | |
|---|---|---|
| EP | 1320389 | 11/2006 |
| WO | WO 01/35885 A1 | 5/2001 |
| WO | WO 01/39582 A1 | 6/2001 |
| WO | WO 02/17981 A1 | 3/2002 |
| WO | WO 2005/049100 A1 | 6/2005 |

* cited by examiner

ABSORBENT ARTICLE INCLUDING A BUFFER COMPOSITION

FIELD OF INVENTION

The present invention generally relates to absorbent sanitary articles for absorption of body fluids and in particular to a sanitary article of this type including a buffer composition adapted to adjust the natural pH of the absorbed body fluid, at the surface of the article, to a pH that is compatible with the pH of skin.

BACKGROUND OF THE INVENTION

Absorbent articles such as sanitary napkins, pantiliners, incontinence articles and adhesive bandages are used to absorb body fluids such as menses, blood, urine and other body fluids.

Different body fluids have a fairly wide pH range, for example menses has pH of about 7.2, blood has a pH of about 7, urine has a pH of about 6.0 to about 7.2, and normal vaginal discharge may range from about 3.8 to about 4.5. Skin typically has a pH of about 5.3. Thus body fluid discharged from the body may have a pH that is significantly different than the pH of skin.

Absorbent articles such as sanitary napkins, pantiliners, incontinence articles and adhesive bandages are arranged in direct contact with the skin during use. Thus, if absorbed body fluids are in contact with skin, particularly over an extended period of time, the skin may become irritated due to the difference in pH of the body fluid and the pH of skin. Therefore, there is a need for an absorbent article that has the ability to absorb body fluids having a wide range of pH and adjust the natural pH of such body fluids, at the body facing surface of the absorbent article, to a pH compatible with the pH of skin.

SUMMARY OF THE INVENTION

In view of the foregoing, the present invention provides an absorbent article including a body facing surface, a liquid permeable cover layer, a liquid impermeable barrier layer, an absorbent core arranged between the cover and barrier, a buffer composition capable of adjusting a pH of body fluids having a natural pH of from about 3.0 to about 8.0 to an adjusted pH of between 4.6 and 6.3 at the body facing surface of the article after such body fluid is absorbed by the absorbent article.

BRIEF DESCRIPTION OF THE DRAWINGS

Examples of embodiments of the present invention will now be described with reference to the drawings, in which.

DETAILED DESCRIPTION OF THE INVENTION

The present invention generally relates to disposable absorbent articles such as sanitary napkins, pantiliners, absorbent products for incontinence, adhesive bandages and other disposable absorbent articles worn close to a wearer's body. Although the invention will be described herein with reference to a pantiliner 10, the invention may be utilized with other disposable sanitary absorbent articles such as sanitary napkins, incontinence products, diapers, and the like.

Absorbent articles according to the present invention effectively absorb body fluids and rapidly adjust the pH of such body fluid from their natural pH to a pH that is compatible with the pH of skin. Specifically, the pH of the absorbed fluid is adjusted such that fluid present at the body facing surface of the article has a pH that is compatible with the pH of skin. For purposes of the present invention "a pH that is compatible with the pH of skin" means a pH of from 4.6 to 6.3.

By adjusting the pH of the absorbed body fluid in this manner, the pH of the fluid is rendered compatible with the pH of skin. In this way any absorbed fluid that comes in contact with the skin will not cause irritation to the skin. This reduction in irritation promotes overall skin health.

Figure 1:
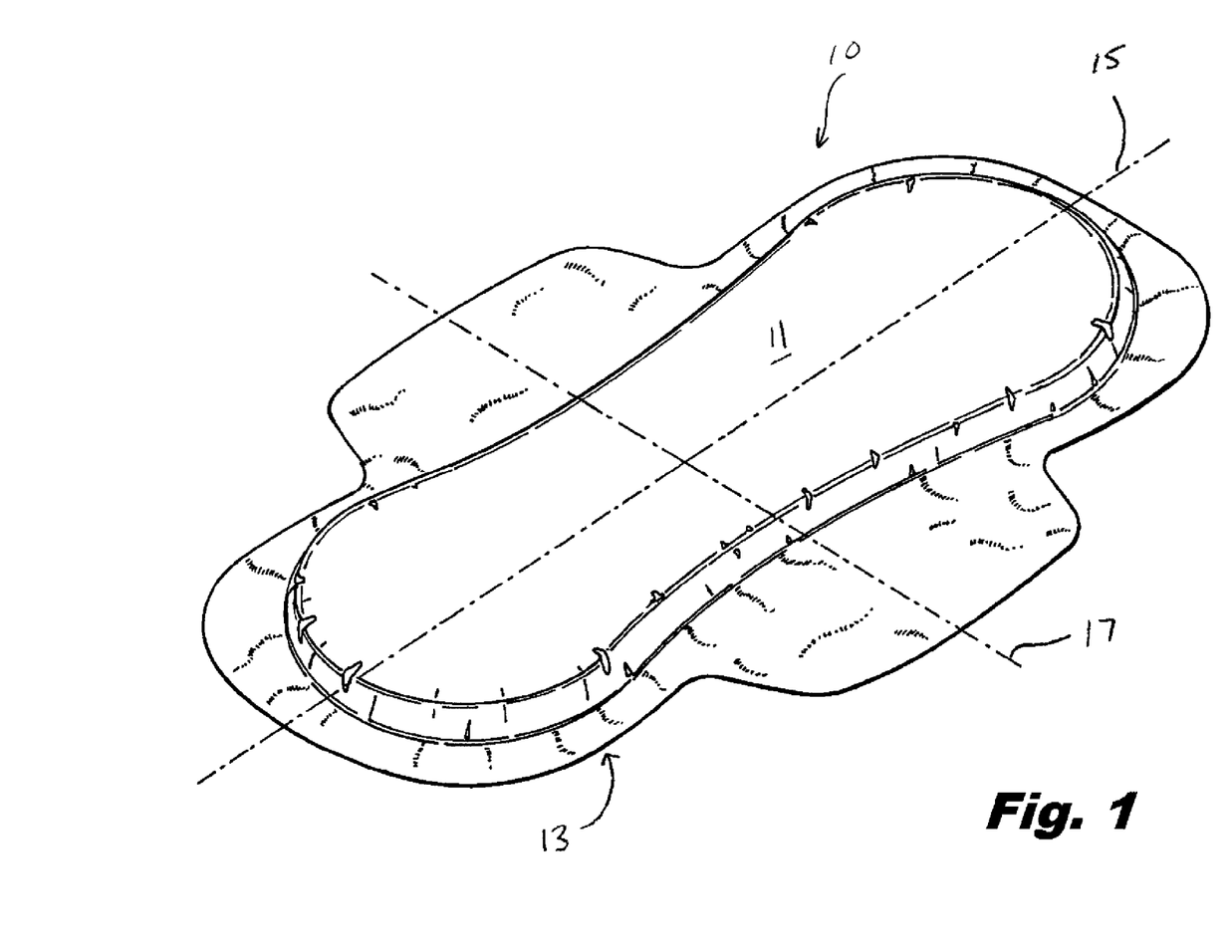
FIG. 1 is a top perspective view of an absorbent article according to the present invention.

As shown in FIG. 1, the present invention according to one embodiment of the invention relates to a pantiliner 10 for absorbing body fluids. The pantiliner 10 includes a body facing surface 11, a garment facing surface 13, a longitudinally extending centerline 15, and a transversely extending centerline 17.

Figure 2:
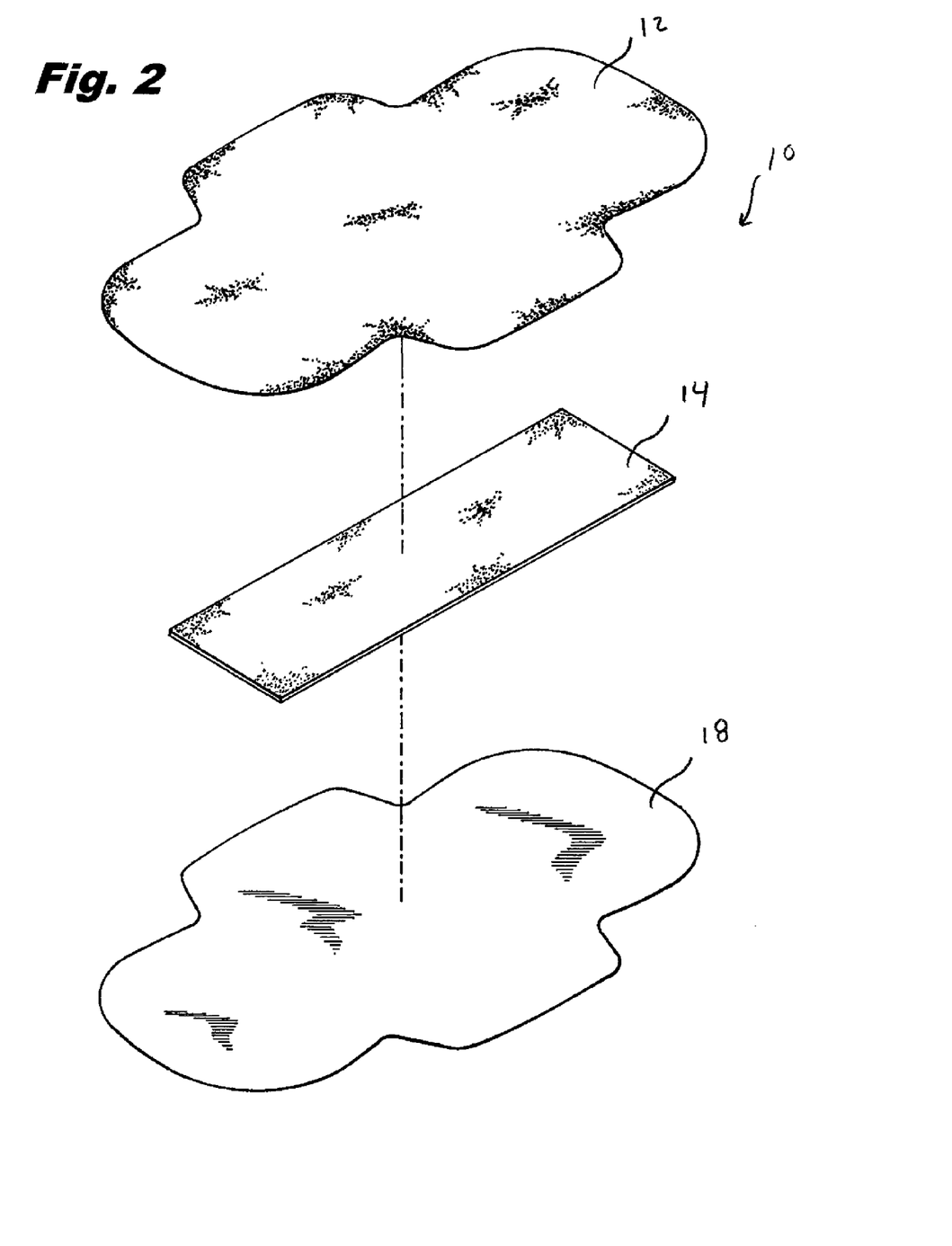
FIG. 2 is an exploded view of the absorbent article shown in FIG. 1 according to a first embodiment of the invention.
Figure 3:
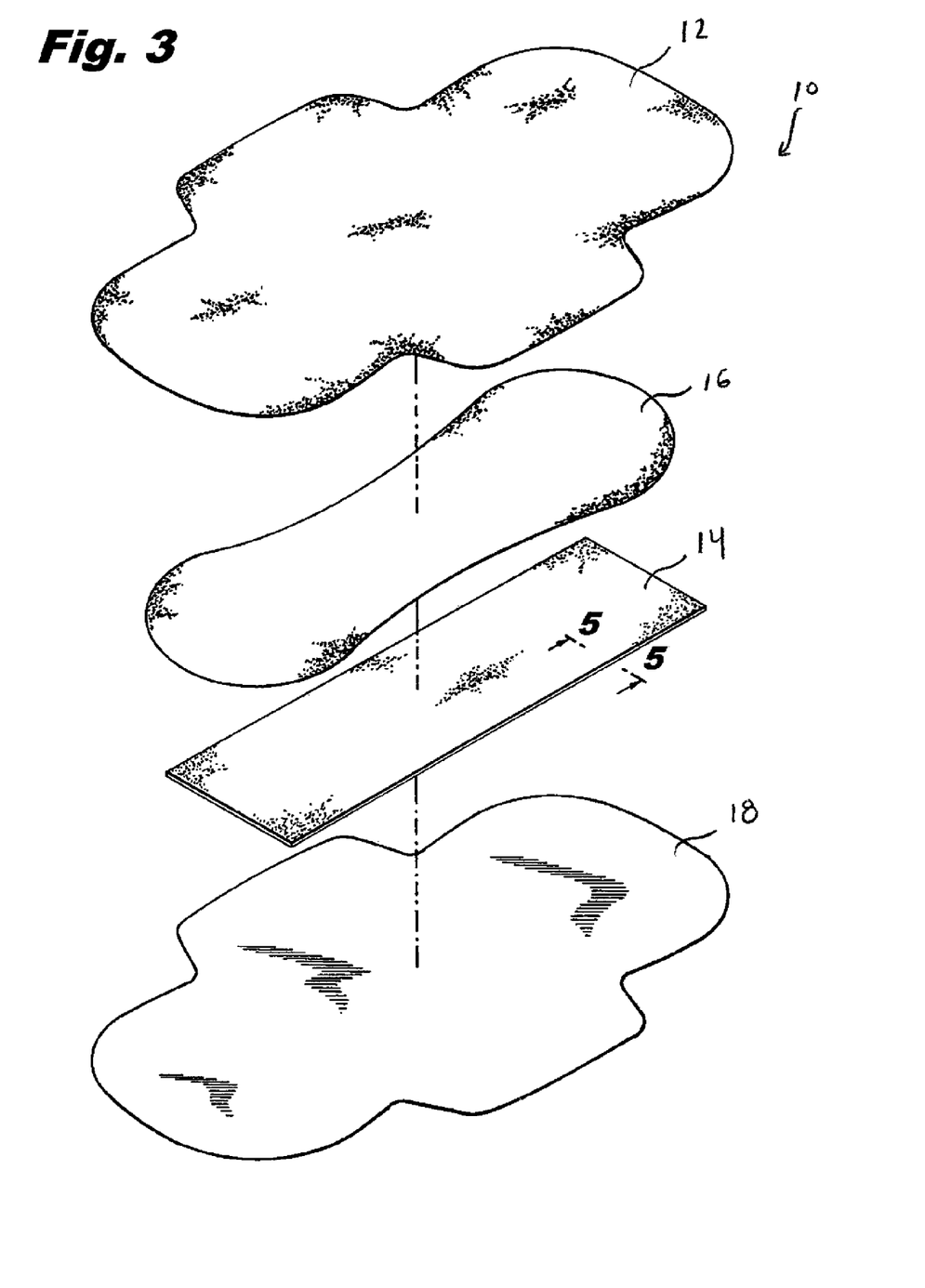
FIG. 3 is an exploded view of the absorbent article shown in FIG. 1 according to a second embodiment of the invention.

As best seen in the exploded view shown in FIG. 2, the pantiliner 10 includes a fluid permeable cover layer 12, an absorbent core 14, and a fluid impermeable barrier layer 18. The pantiliner 10 according to a second embodiment of the invention may further include, as shown in FIG. 3, a transfer layer 16 arranged between the cover layer 12 and the absorbent core 14.

Figure 4:
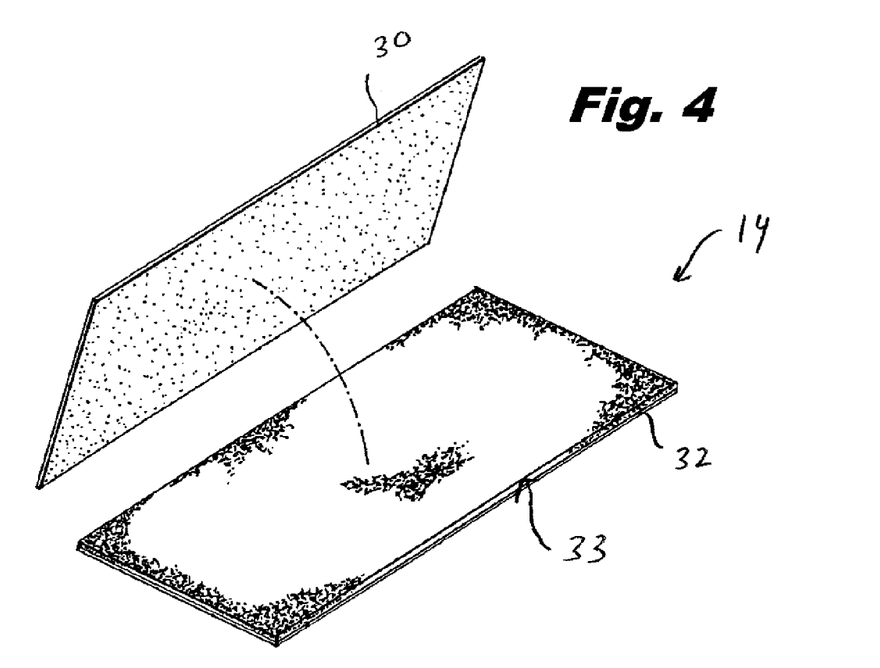
FIG. 4 is an exploded view of an absorbent core employed in the absorbent article shown in FIG. 1.
Figure 5:
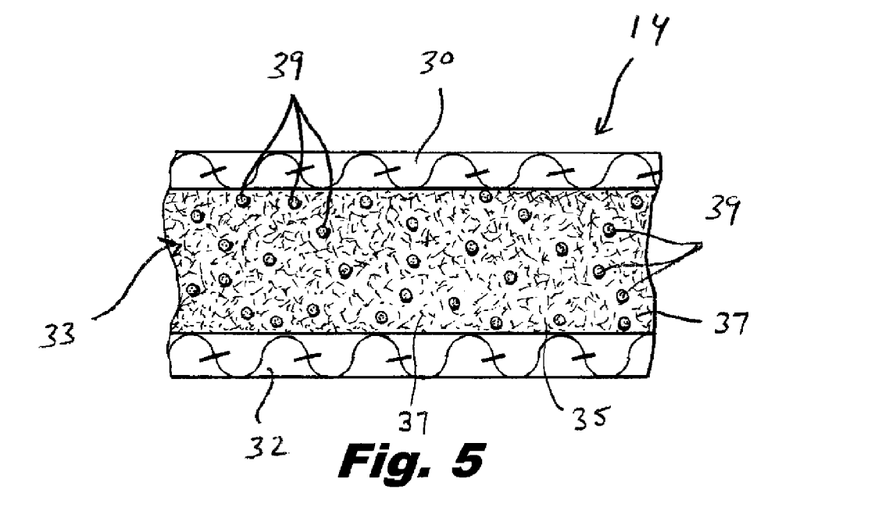
FIG. 5 is a sectional view of the absorbent core taken along line 5-5 in FIG. 3.

In a preferred embodiment of the invention, shown in FIGS. 4 and 5, the absorbent core 14 is a multilayer construct including a first absorbent layer 30, a second absorbent layer 32, and an absorbent mixture 33 arranged between the layers 30, 32. As described in greater detail below (See, "Absorbent Core" section below), the absorbent mixture 33 includes a mixture of superabsorbent polymer 35 and adhesive 37 arranged between the substrate layers 30, 32.

The pantiliner 10 further includes a buffer composition 39 adapted to adjust the pH of absorbed body fluids from their natural pH to an adjusted pH of from 4.6 to 6.3 as measured at the body facing surface 11 of the pantiliner. The buffer composition 39 employed in the present invention is effective at adjusting the pH of body fluids have a wide range of natural pH, e.g. from about 3.0 to about 8.0, to the adjusted range described above of between 4.6 to 6.3 as measured at the body facing surface 11 of the pantiliner. By adjusting the pH of the absorbed body fluid in this manner, the pH of the fluid is rendered compatible with the pH of skin. In this way any absorbed fluid that comes in contact with the skin will not cause irritation to the skin.

Although not shown in the Figures, the areas of the pantiliner 10 in which the buffer composition 39 is located may be colored a different color than the remainder of the absorbent article. For example, the areas in which the buffer composition 39 is located may be colored blue while the remainder of the pantiliner 10 is generally white. By coloring those areas where buffer composition 39 is located a different color than the remainder of the pantiliner 10, a skin health benefit is visually communicated to a potential user of the absorbent article. The color may be imparted to the pantiliner 10 by providing a color (e.g., ink) to one or more of the cover layer 12, transfer layer 16, absorbent core 14, and barrier layer 18.

Cover Layer

The cover layer 12 may be a relatively low density, bulky, high-loft non-woven web material. The cover layer 12 may be composed of only one type of fiber, such as polyester or polypropylene or it may include a mixture of more than one fiber. The cover may be composed of bi-component or conjugate fibers having a low melting point component and a high melting point component. The fibers may be selected from a variety of natural and synthetic materials such as nylon, polyester, rayon (in combination with other fibers), cotton, acrylic fiber and the like and combinations thereof. Preferably, the cover layer 12 has a basis weight in the range of about 10 gsm to about 75 gsm.

Bi-component fibers may be made up of a polyester layer and a polyethylene sheath. The use of appropriate bi-component materials results in a fusible non-woven fabric. Examples of such fusible fabrics are described in U.S. Pat. No. 4,555,430 issued Nov. 26, 1985 to Chicopee. Using a fusible fabric increases the ease with which the cover layer may be mounted to the absorbent layer and/or to the barrier layer.

The cover layer 12 preferably has a relatively high degree of wettability, although the individual fibers comprising the cover may not be particularly hydrophilic. The cover material should also contain a great number of relatively large pores. This is because the cover layer 12 is intended to take-up body fluid rapidly and transport it away from the body and the point of deposition. Therefore, the cover layer contributes little to the time taken for the pantiliner to absorb a given quantity of liquid (penetration time).

Advantageously, the fibers which make up the cover layer 12 should not lose their physical properties when they are wetted, in other words they should not collapse or lose their resiliency when subjected to water or body fluid. The cover layer 12 may be treated to allow fluid to pass through it readily. The cover layer 12 also functions to transfer the fluid quickly to the underlying layers of the pantiliner. Thus, the cover layer 12 is advantageously wettable, hydrophilic and porous. When composed of synthetic hydrophobic fibers such as polyester or bi-component fibers, the cover layer 12 may be treated with a surfactant to impart the desired degree of wettability.

Alternatively, the cover layer 12 can also be made of polymer film having large pores. Because of such high porosity, the film accomplishes the function of quickly transferring body fluid to the inner layers of the underlying absorbent layers.

The cover layer 12 may be attached to the underlying absorbent layers 14 and 16, and/or the barrier layer 18, by adhesion and/or other suitable means know to those of skill in the art.

Absorbent Core

The absorbent core 14 may be composed of fibrous materials, such as wood pulp, polyester, rayon, flexible foam, or the like, or combinations thereof. The absorbent core 14 may also optionally include a superabsorbent polymer (SAP) material. The absorbent core 14 may also comprise thermoplastic fibers for the purpose of stabilizing the layer and maintaining its structural integrity. The absorbent core 14 may be treated with surfactant on one or both sides in order to increase its wettability, although generally the absorbent core 14 is relatively hydrophilic and may not require treatment. The absorbent core 14 is preferably bonded on both sides to the adjacent layers, e.g. the cover layer 12 (or transfer layer 16 if such a layer is employed) and the underlying barrier layer 18.

The absorbent core 14 may comprise a single layer of material or may comprise multiple layers. The absorbent core 14 may comprise a blend or mixture of cellulosic fibers and superabsorbent polymer disposed therein. Cellulosic fibers that can be used in the first absorbent layer 14 are well known in the art and include wood pulp, cotton, flax and peat moss. Wood pulp is preferred. Pulps can be obtained from mechanical or chemi-mechanical, sulfite, kraft, pulping reject materials, organic solvent pulps, etc. Both softwood and hardwood species are useful. Softwood pulps are preferred. It is not necessary to treat cellulosic fibers with chemical debonding agents, cross-linking agents and the like for use in the present material. Some portion of the pulp may be chemically treated as discussed in U.S. Pat. No. 5,916,670 to improved flexibility of the product. Flexibility of the material may also be improved by mechanically working the material or tenderizing the material.

The first absorbent layer 14 can contain any superabsorbent polymer (SAP) which are well known in the art. For the purposes of the present invention, the term "superabsorbent polymer" (or "SAP") refers to materials which are capable of absorbing and retaining at least about 10 times their weight in body fluids under a 0.5 psi pressure. The superabsorbent polymer particles of the invention may be inorganic or organic crosslinked hydrophilic polymers, such as polyvinyl alcohols, polyethylene oxides, crosslinked starches, guar gum, xanthan gum, and the like. The particles may be in the form of a powder, grains, granules, or fibers. Preferred superabsorbent polymer particles for use in the present invention are crosslinked polyacrylates, such as the product offered by Sumitomo Seika Chemicals Co., Ltd. Of Osaka, Japan, under the designation of SA70N and products offered by Stockhausen Inc. In a specific example, the absorbent core 14 may comprise from 90% to about 40% percent cellulosic fiber, about 10% to about 60% SAP. The absorbent core 14 may comprise a material manufactured by using air-laying means well known in the art.

In one embodiment of the invention the first absorbent layer 14 is relatively thin, high swelling absorbent material such as the absorbent composite material sold under the trade name NOVATHIN® available from EAM Corporation located in Jessup, Ga., U.S.A.

In a preferred embodiment of the invention, shown in FIG. 4, the absorbent core 14 is a multilayer construct including a first absorbent layer 30, a second absorbent layer 32, and an absorbent mixture 33 arranged between the layers 30, 32. The absorbent mixture 33 includes a mixture of superabsorbent polymer 35 and adhesive 37 arranged between the substrate layers 30, 32.

In a specific example, the first absorbent layer 30 and second absorbent layer 32 may be constructed from pulp tissue commercially available from Little Rapids Corporation, Shawano, Wis. In another specific example, the first absorbent layer and the second absorbent layer 32 may be constructed from pulp tissue commercially available from pulp tissue commercially available from Cellu Tissue in East Hartford, Conn. under product code 3207.

Preferably the absorbent mixture 33 includes between about 50% to about 98% superabsorbent polymer by weight and between about 50% and 2% adhesive by weight. Preferred superabsorbents for use in the present invention include Aqua Keep BA40B and SA70 commercially available from Sumitomo Seika Chemicals Co., Ltd., Osaka Japan.

Preferably a holt melt adhesive is utilized as the adhesive in the mixture 33. A suitable commercially available adhesive comprises HB Fuller NW 1023AA hot melt adhesive, commercially available from HB Fuller Company, St. Paul, Minn.

The mixture 33 is preferably free of any fibrous material, such as cellulosic or synthetic fibrous material. In preferred embodiments of the present invention, the mixture 33 is composed entirely from superabsorbent polymer and adhesive.

The mixture 33 may be applied between the layers 30, 32 in two separate steps, e.g. the adhesive and superabsorbent may be applied sequentially, or alternatively the adhesive and superabsorbent may be applied substantially at the same time. Any suitable means known to those in the art may be used to apply the mixture 33 between the layers 30, 32. A suitable process for applying the mixture 33 is disclosed in pending U.S. patent application Ser. No. 12/683,260, the contents of which are incorporated herein by reference.

Transfer Layer

The pantiliner 10 according to the present invention may optionally include, as shown in FIG. 3, a transfer layer 16 arranged between the cover layer 12 and the absorbent core 14.

The transfer layer 16 provides the means of receiving body fluid from the cover layer 12 and holding it until the underlying absorbent core 14 has an opportunity to absorb the fluid.

The transfer layer 16 is, preferably, more dense than and has a larger proportion of smaller pores than the cover layer 12. These attributes allow the transfer layer 16 to contain body fluid and hold it away from the outer side of the cover layer 12, thereby preventing the fluid from rewetting the cover layer 12 and its surface. However, the transfer layer 16 is, preferably, not so dense as to prevent the passage of the fluid through the transfer layer 16 into the underlying absorbent core 14. These types of absorbent layers are commonly known as fluid transfer layers or acquisition layers.

The transfer layer 16 may be composed of fibrous materials, such as wood pulp, polyester, rayon, flexible foam, or the like, or combinations thereof. The transfer layer 16 may also comprise thermoplastic fibers for the purpose of stabilizing the layer and maintaining its structural integrity. The transfer layer 16 may be treated with surfactant on one or both sides in order to increase its wettability, although generally the transfer layer 16 is relatively hydrophilic and may not require treatment. The transfer layer 16 is preferably bonded on both sides to the adjacent layers, i.e. the cover layer 12 and an underlying absorbent core 14. Examples of suitable transfer layers include a through air bonded pulp sold by BUCKEYE of Memphis Tenn. under the designation VIZORB 3008 and STAPPEL45, a 60/40 polypropylene/polyethylene 45 gsm material available through Shalag Industries, Ltd. of Galilee, Israel.

Barrier Layer

Underlying the absorbent core 14 is a barrier layer 18 comprising liquid-impervious film material so as to prevent liquid that is entrapped in the absorbent core 14 from egressing the pantiliner and staining the wearer's undergarment. The barrier layer 18 is preferably made of polymeric film, although it may be made of liquid impervious, air-permeable material such as repellent-treated non-woven or micropore films or foams.

The barrier layer 18 may be breathable, i.e., permits vapor to transpire. Known materials for this purpose include nonwoven materials and microporous films in which microporosity is created by, inter alia, stretching an oriented film. Single or multiple layers of permeable films, fabrics, melt-blown materials, and combinations thereof that provide a tortuous path, and/or whose surface characteristics provide a liquid surface repellent to the penetration of liquids may also be used to provide a breathable backsheet. The cover layer 12 and the barrier layer 18 are preferably joined along their marginal portions so as to form an enclosure or flange seal that maintains the absorbent core 14 captive. The joint may be made by means of adhesives, heat-bonding, ultrasonic bonding, radio frequency sealing, mechanical crimping, and the like and combinations thereof.

Positioning adhesive may be applied to a garment facing surface 13 of the barrier layer 18 for securing the pantiliner 10 to a garment during use. The positioning adhesive may be covered with removable release paper so that the positioning adhesive is covered by the removable release paper prior to use.

Absorbent articles of this invention may or may not include wings, flaps or tabs for securing the absorbent article to an undergarment. Wings, also called, among other things, flaps or tabs, and their use in sanitary protection articles is described in U.S. Pat. No. 4,687,478 to Van Tilburg; U.S. Pat. No. 4,589,876 also to Van Tilburg, U.S. Pat. No. 4,900,320 to McCoy, and U.S. Pat. No. 4,608,047 to Mattingly. The disclosures of these patents are incorporated herein by reference in their entirety. As disclosed in the above documents, wings are generally speaking flexible and configured to be folded over the edges of the underwear so that the wings are disposed between the edges of the underwear.

Buffer Composition

The pantiliner 10 further includes a buffer composition 39 adapted to adjust the pH of absorbed body fluids from their natural pH to an adjusted pH from 4.6 to 6.3 measured at the body facing surface 11 of the pantiliner 10. By adjusting the pH of the absorbed body fluid in this manner, the pH of the fluid is rendered compatible with the pH of skin. In this way any absorbed fluid that comes in contact with the skin will not cause irritation to the skin.

Buffer compositions typically include a weak acid and its salts or a weak base and its salts. Suitable buffer compositions for use in the present invention include, but are not limited to a mixture of sodium citrate and citric acid, a mixture of sodium acetate and acetic acid, a mixture of dibasic sodium phosphate and citric acid, and the like. Where the buffer composition is sodium citrate and citric acid, the ratio of sodium citrate to citric acid may range from 6.2 to 1 to 7.2 to 1 (weight to weight). The amount of buffer composition in the absorbent article will vary depending on the amount of body fluid anticipated to contact the absorbent article, the pH of the body fluid, and the buffer composition being utilized, but typically may range from 0.1 g to 5 g.

It has been discovered that the buffer composition 39 performs better when it does not contact the cover layer 12 directly (in the dry state). The buffer composition 39 may be prepared in a dry state, or in a liquid state which is dried after application to the absorbent article through the use of heat and/or air. The buffer composition 39 may be added during the process of making the absorbent core 14 or during the process of making the absorbent article (e.g. the composition may be added on top of the core 14 and beneath a transfer layer 16).

In one embodiment of the invention present invention the buffer composition 39 may be arranged between the first absorbent layer 30 and second absorbent layer 32 of the absorbent core 14 as shown in FIG. 5. For example, the buffer composition 39 may be arranged on top of the absorbent mixture 33 after such mixture 33 has been applied to one of the absorbent layers 30 and 32. In another embodiment, the buffer composition 39 could be incorporated into the absorbent mixture 33 by pre-mixing the buffer with the superabsorbent polymer prior to application to one of the absorbent layers 30 and 32. In another embodiment, the buffer composition 39 may be arranged between the absorbent core 14 and the transfer layer 16 of the pantiliner 10.

Test Procedures

Absorbent articles according to the present invention possess the unique ability to absorb body fluids having a wide range of natural pH and adjust the pH of the absorb fluid to a pH level that is compatible with the pH of skin. The test procedure set forth below highlights this property. Prior to conducting any of the described test procedures described below the test product should be conditioned for two hours at 21+/−1° C. and 50+/−2% humidity. Samples were tested by adding a test fluid to the top surface of the article. The pH of the solution on the top surface of the article was measured after 1 minute using a Mettler-Toledo Sevengo pH meter having a surface probe. The pH meter is commercially available under product code SG2-B from Mettler-Toledo, Inc., Columbus, Ohio. The surface probe is commercially available under product code 51343157 from Mettler-Toledo, Inc., Columbus, Ohio.

EXAMPLES

Inventive Examples

Inventive examples of a pantiliner according to the present invention were constructed as follows:

A 50 gsm spunlace nonwoven cover layer from a blend of 70% polyester terephthalate fibers (R-298G Polyester staple fiber from Reliance Industries, LTD.) and 30% polypropylene fibers (SL050-JL04-F from FibreVisions) and was spray coated on one surface with 5 gsm of hot melt adhesive commercially available as NW 1023 AA from H.B. Fuller located in St. Paul, Minn. An absorbent core was prepared by taking two 17 gsm pulp tissue layers commercially available from Cellu Tissue in East Hartford, Conn. under product code 3207 and applying a mixture of 20.5 gsm of superabsorbent polymer commercially available as Aqua Keep BA40B from Sumitomo Seika Chemicals Co., Ltd., Osaka, Japan and 3.5 gsm of NW 1023 AA hot melt adhesive, commercially available from HB Fuller Company, St. Paul, Minn., between the tissue layers.

Hot melt adhesive (NW 1023 AA, commercially available from HB Fuller Company, St. Paul, Minn.) was spiral spray coated onto the absorbent core on a top surface thereof in the amount of 3.4 gsm to bond the first absorbent layer to a transfer layer arranged between the cover and the core. The transfer layer was formed from STAPPEL45, a 60/40 polypropylene/polyethylene 45 gsm material commercially available from Shalag Industries, Ltd., Galilee, Israel.

A 0.7 mil polymeric film PP XP3471A back sheet commercially available from Pliant Corporation, Schaumburg, Ill., was placed on the garment facing side of the absorbent core and laminated to the bottom surface of the absorbent core by slot coating the upper surface of the barrier film with H.B. Fuller NW-1023AA at 5.3 gsm prior to placing the absorbent core thereon. The final composite was crimped along the peripheral edge of the article and final cut. Positioning adhesive was applied to the exterior surface of the barrier film by slot coating Bostik H20028F adhesive at 16.2 gsm and the adhesive surface was covered with a conventional silicone coated release liner.

Inventive Samples 3 and 4 in the chart set forth below had 0.44 g of a buffer composition including sodium citrate dihydrate (USP/FCC purchased from Archer Daniels Midland company, Decatur, Ill.) and citric acid anhydrous (FG powder also purchased from Archer Daniels Midland company) in a ratio of 6.7 to 1 by weight placed beneath the transfer layer and above the core.

Samples 1 and 2 did not contain buffer composition and were tested as controls.

Comparative Example #1

Samples 5 and 6 were Kotex Fresh pH 5.5 liners commercially available from Kimberly-Clark Limited, Hong Kong.

Test Fluids

Each of the product samples described above were tested using the two test fluids specified below.

(1) A low pH formulation was prepared by combining deionized water and citric acid. The pH of the solution was measured to be 3.6.

(2) A synthetic urine formulation was prepared by combining the following materials in a beaker and stirring: 0.2 g potassium chloride, 0.2 g sodium sulphate, 0.085 g ammonium phosphate monobasic, 0.015 g ammonium phosphate dibasic, 0.019 g calcium chloride, 0.023 g magnesium chloride, and 99.458 g distilled water. The pH of the solution was measured to be 7.1.

Each of the product samples were tested according to the test method described above using each of the test fluids. The amount of fluid applied to each product sample is specified in Table 1 below. The measured pH of the absorbed fluid after 1 minute is also set forth in the chart below.

TABLE 1

| Sample | Challenge Fluid | pH after 1 minute |
|---|---|---|
| 1 (Control) | 3 ml low pH fluid | 3.8 |
| 2 (Control) | 3 ml synthetic urine | 7.1 |
| 3 (Inventive) | 3 ml low pH fluid | 5.3 |
| 4 (Inventive) | 3 ml synthetic urine | 6.1 |
| 5 (Comparative) | 3 ml low pH fluid | 4.2 |
| 6 (Comparative) | 3 ml synthetic urine | 7.0 |

As illustrated in the table provided above, absorbent articles according to the present invention can rapidly adjust the pH of absorbed body fluids having a wide range of natural pH to an adjusted pH level that is compatible with the pH of skin.

The invention claimed is:

1. An absorbent article comprising:
an absorbent article length;
an absorbent article width;
a body facing surface;
a liquid permeable cover layer;
a liquid impermeable barrier layer;
an absorbent core arranged between the cover layer and the barrier layer, the absorbent core, the absorbent core having an absorbent core length and an absorbent core width that are less than the absorbent article length and the absorbent article width, respectively, the absorbent core comprising:
a first absorbent layer;
a second absorbent layer; and a superabsorbent polymer and adhesive mixture arranged between the first absorbent layer and the second absorbent layer, the core comprising between about 50% and 98% of the superabsorbent polymer and between about 2% and about 50% of the adhesive, the superabsorbent polymer and adhesive mixture is free from fibrous material; and a buffer composition capable of adjusting a pH of body fluids having a natural pH of from about 3.0 to about 8.0 to an adjusted pH of between 4.6 and 6.3 at the body facing surface of the article after such body fluid is absorbed by the absorbent article, the buffer composition arranged between said first absorbent layer and the second absorbent layer, wherein the buffer composition, in its dry state, does not contact the cover layer, wherein the buffer composition is in an amount of about 0.1 g to about 5.0 g, wherein a location of the buffer composition has a color different from the remainder of the absorbent article to visually communicate a skin health benefit, the coloring including ink provided only in a region having the buffer composition such that the color viewable from the body facing surface.

2. The absorbent article according to claim 1, wherein the buffer composition comprises sodium citrate and citric acid.

3. The absorbent article according to claim 2, wherein the ratio of sodium citrate to citric acid is form from 6.2:1 to 7.2:1.

4. The absorbent article of claim 1, wherein the adjusted pH of the body facing surface is achieved about a minute after the body fluid came into contact with the body facing surface.

5. The absorbent article of claim 1, wherein the buffer composition is applied only to the absorbent core.

6. The absorbent article of claim 1, wherein the superabsorbent polymer and adhesive mixture further comprises the buffer composition.

7. The absorbent article of claim 1, wherein the adjusted pH of the body facing surface is achieved about a minute after the body fluid came into contact with the body facing surface.

8. The absorbent article of claim 1, wherein the absorbent core is treated with surfactant on a first side of the absorbent core that is between the absorbent core and the first absorbent layer and on a second side of the absorbent core that is between the absorbent core and the second absorbent layer.

9. The absorbent article of claim 1, further comprising:
a transfer layer arranged between, and bonded to, the cover layer and the absorbent core,
wherein the transfer layer is more dense than the cover layer and has a larger proportion of pores than the cover layer,
wherein the transfer layer is composed of at least one fibrous material, and
wherein the transfer layer includes thermoplastic fibers.

10. The absorbent article of claim 9, wherein the transfer layer is treated with surfactant on a first side of the transfer layer that is between the transfer layer and the cover layer and on a second side of the transfer layer that is between the transfer layer and the absorbent core.

11. The absorbent article of claim 1, wherein the barrier layer includes a plurality of layers of polymeric film or a repellant-treated non-woven micropore film or foam, and wherein the barrier layer is configured to permit vapor to transpire, and wherein the layers provide a tortuous path with respect to a liquid.

12. The absorbent article of claim 1, wherein the liquid permeable cover is porous.

13. The absorbent article according to claim 12, wherein the porous liquid permeable cover comprises a foam material having large pores.

14. An absorbent article comprising:
an absorbent article length;
an absorbent article width;
a liquid permeable cover layer having a body facing surface;
a liquid impermeable barrier layer;
an absorbent core arranged between the cover layer and the barrier layer, the absorbent core having an absorbent core length and an absorbent core width that are less than the absorbent article length and the absorbent article width, respectively, the absorbent core, the absorbent core comprising:
a first absorbent layer;
a second absorbent layer; and
a superabsorbent polymer and adhesive mixture arranged between the first absorbent layer and the second absorbent layer, the core comprising between about 50% and 98% of the superabsorbent polymer and between about 2% and about 50% of the adhesive, the superabsorbent polymer and adhesive mixture is free from fibrous material; and
a buffer composition capable of adjusting a pH of body fluids, wherein the buffer composition is only applied to the absorbent core and arranged between the first absorbent layer and the second absorbent; and
wherein the buffer composition, in its dry state, does not contact the body facing surface; and
wherein the buffer composition is in amount of between about 0.1 g and about 5.0 g,
wherein a location of the buffer composition has a color different from the remainder of the absorbent article to visually communicate a skin health benefit, the coloring including ink provided only in a region having the buffer composition such that the color viewable from the body facing surface.

15. The absorbent article of claim 14, wherein the buffer composition is capable of adjusting a pH of body fluids having a natural pH of from about 3.0 to about 8.0 to an adjusted pH of between 4.6 and 6.3 at the body facing surface of the article after such body fluid is absorbed by the absorbent article.

16. The absorbent article of claim 15, wherein the ratio of sodium citrate to citric acid is from 6.2:1 to 7.2:1.

17. The absorbent article of claim 14, wherein the superabsorbent polymer and adhesive mixture further comprises the buffer composition.

18. The absorbent article of claim 14, wherein the buffer composition comprises sodium citrate and citric acid.

* * * * *